United States Patent [19]
Schneider

[11] Patent Number: 5,547,375
[45] Date of Patent: Aug. 20, 1996

[54] SUCTION DEVICE FOR DENTAL TREATMENT UNITS

[76] Inventor: Hans-Georg Schneider, Bendigstr. 09, 12557 Berlin, Germany

[21] Appl. No.: 296,698

[22] Filed: Aug. 26, 1994

[30] Foreign Application Priority Data

Aug. 27, 1993 [DE] Germany .......................... 43 29 352.2

[51] Int. Cl.⁶ ............................................. A61C 17/06
[52] U.S. Cl. ............................................................ 433/96
[58] Field of Search .............................. 433/91, 93, 94, 433/95, 96; 138/106, DIG. 8, 111

[56] References Cited

U.S. PATENT DOCUMENTS

| | | | |
|---|---|---|---|
| 1,388,312 | 8/1921 | Seeger | 433/96 |
| 1,458,916 | 6/1923 | Sampson | 138/106 |
| 2,853,262 | 9/1958 | Reimann | 138/106 |
| 5,263,646 | 11/1993 | McCauley | 138/DIG. 8 |

FOREIGN PATENT DOCUMENTS

| | | | |
|---|---|---|---|
| 575950 | 12/1993 | European Pat. Off. | 433/91 |
| 4307496 | 8/1993 | Germany . | |
| 4306450 | 5/1994 | Germany | 433/91 |

Primary Examiner—Cary E. O'Connor
Attorney, Agent, or Firm—Young & Basile, P.C.

[57] ABSTRACT

A suction device with a suction hose and suction cannula for dental treatment units for the sucking off of the spray mist during dental treatment processes in which the suction hose is placed on or in a flexible tube, which is movable in three-dimensional manner, so that the suction hose can be brought into the treatment position and can be positioned there without any need for a dental nurse.

10 Claims, 3 Drawing Sheets

SUCTION DEVICE FOR DENTAL TREATMENT UNITS

BACKGROUND OF THE DISCLOSURE

1. Field of the Invention

The invention relates to a suction device for dental treatment units having a suction hose and a suction cannula.

2. Description of the Art

For dental treatment units, suction devices are known for use in specific working processes, e.g., cavity preparation or stump preparation for crowns and the like, where cutting, grinding, polishing or drilling tools are used in a constricted space for a long time. The suction devices are used for sucking off dust occurring in the case of high-speed drilling of hard dental substances, fillings or stopping materials, etc., which with the water spray supplied as the coolant form a suspension mist and which through whirled up microorganisms from the plaque, saliva and oral mucosa secretions form a health hazard for the patient, dentist and dental nurse. The known suction device comprises an approximately 25 mm thick, elastic plastic hose and an approximately 10 mm thick suction cannula, whose end is flat, i.e., slotlike, and which is used for the suction of the spray mist of the dental turbine with which a hard metal cutting tool or a drilling tool is operated at high speed. The suction hose leads into an intake connection integrated into the dental treatment unit, which is connected to a fixed suction installation.

In the prior art suction device, which is installed on the dental treatment unit, the suction hose with the suction cannula is guided and manually positioned by the dental nurse or dentist. It is therefore necessary during cutting or drilling operations in the mouth for a dental nurse to always be present for suction purposes, otherwise the dentist is forced to hold the suction connection himself, so that he is only able to work with one hand in the mouth for the preparation operations. He then does not have a second hand available for guiding the dental mirror, e.g., for keeping the field of view free.

The problem of the invention is therefore to provide a suction device for the spray mist in the case of dental drilling and cutting processes in the oral cavity, so that for certain operations the dentist no longer requires the assistance of a dental nurse.

SUMMARY OF THE INVENTION

Due to the fact that, according to the present invention, the suction hose is located in or on a three-dimensionally movable flexible tube, the activity of the dental nurse is replaced by a flexible support to which the suction cannula is fixed which, once in the desired position, maintains said position in a non-manual or "mechanical" manner.

Through different constructions and associations between the flexible tube and the suction hose, it is possible both to provide a suction device fixed to the dental treatment unit and also to reequip an existing suction device and then the flexible tube can be fixed with a clamping device or the like to the dental treatment unit. Through the provision of a separate flexible tube to which the suction hose can be fixed by suction clips, it is possible to rapidly fit or detach the suction device.

BRIEF DESCRIPTION OF THE DRAWING

Embodiments of the invention are described in greater detail hereinafter relative to the attached drawings, wherein.

DESCRIPTION OF THE PREFERRED EMBODIMENTS

Figure 1:
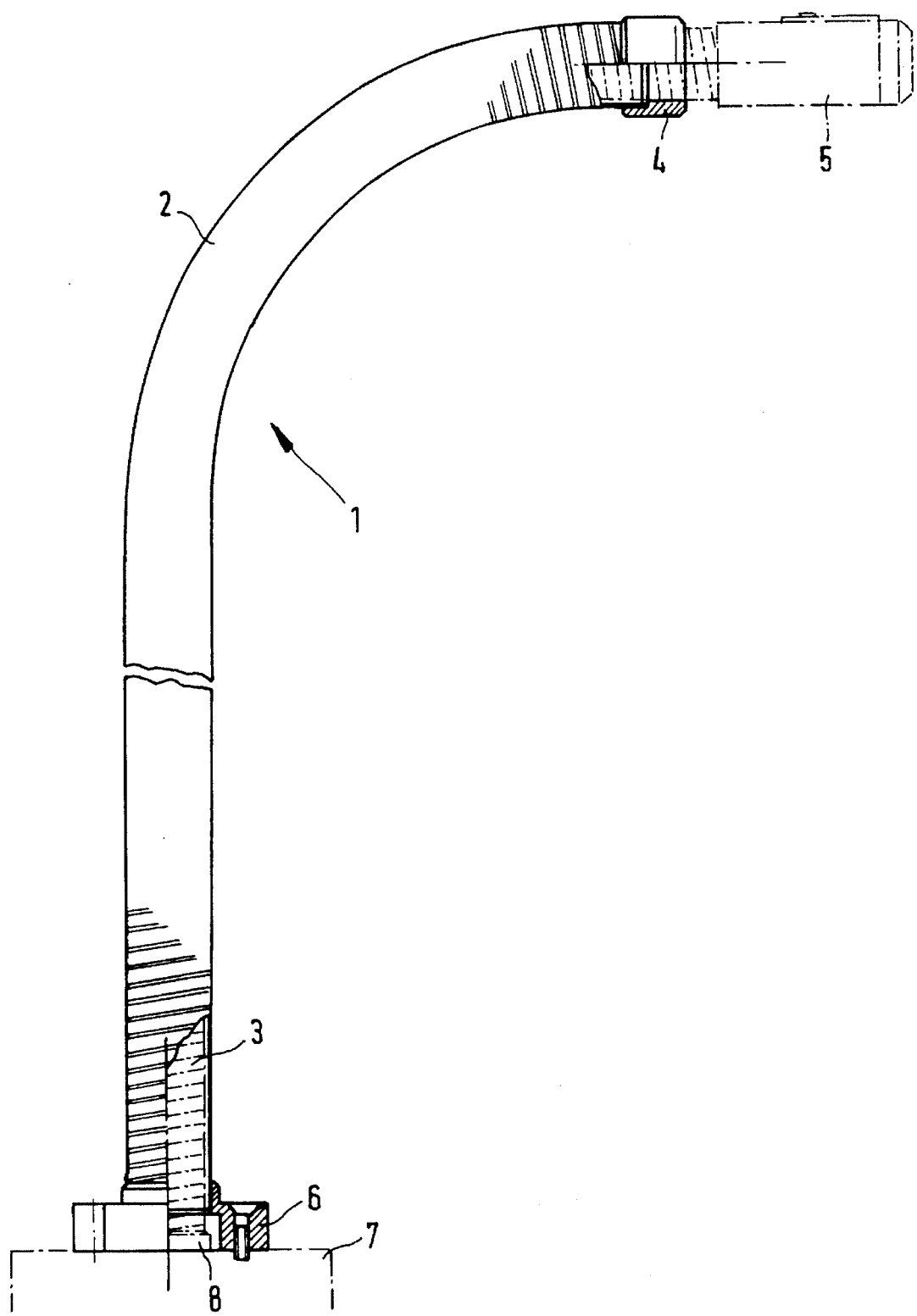
FIG. 1 is a partially cross sectioned side elevational view of a suction device according to a first embodiment of the invention.

The suction device 1 shown in FIG. 1 has a flexible tube 2, e.g., with an internal diameter of 24 mm, in which is placed a plastic suction hose 3, e.g., having a diameter of 22 mm, and firmly integrated into the former. The term "flexible tube" is understood to mean a tube which can be bent in all directions and retains the bent state until it is bent again and brought into another position. Such a tube can, for example, be constructed as a corrugated or grooved plastic tube, which can also be chromium-plated. The suction hose 3 passes within and beyond the end of the flexible tube 2, which is terminated with a tube end piece 4, and carries a standard plug connection 5 for a suction cannula. The other end of the flexible tube 2 is fixed to the dental treatment unit 7 by means of an attachment flange 6 connected thereto. The attachment flange 6 engages over a suction connection 8 placed firmly on the treatment unit 6 and into which is introduced the suction hose 3. The suction hose 3 is connected to a fixed installed suction plant, which produces a vacuum when a switch is operated. Such a switch is preferably constructed with a suction plant according to the invention in the form of a foot or pedal switch, so that by means of the latter the dentist can control a solenoid valve enabling the suction process to be switched on and off.

In operation, the flexible tube 2 with the suction hose 3 is manually brought into the operating position, e.g., the drilling position, and remains positioned in the immediate vicinity of the tooth to be treated. When the pedal switch is operated by the dentist a vacuum is produced by the suction plant and the coolant sprayed in the vicinity of the drilling process, mixed with the drilling residues, is removed from the oral cavity by suction.

The suction device according to FIG. 1 is provided in addition to that according to the prior art which is continuously held by the dental nurse during the treatment operation.

Figure 2:
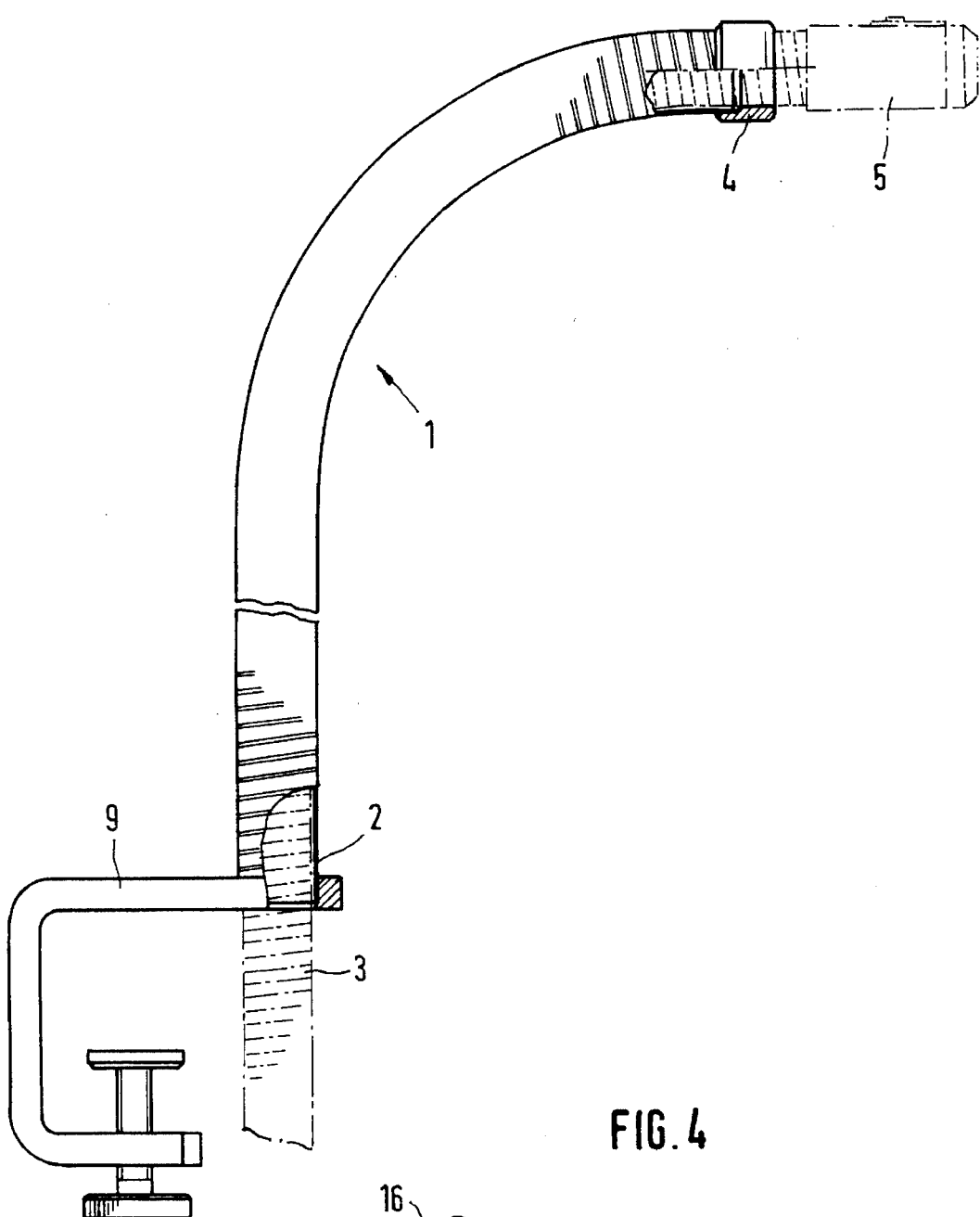
FIG. 2 is a partially cross sectioned side elevational view of a suction device according to a second embodiment of the invention.

FIG. 2 shows another embodiment, which differs from that of FIG. 1 in that use is made of the suction hose of the standard suction device provided on the dental treatment unit, the suction hose 3 being guided by the flexible tube 2. The flexible tube 2 is anchored, e.g., bonded in a screw clamp 9, which fixes the suction device 1 to the dental treatment unit. This embodiment is suitable for the reequipping of dental treatment units and, if necessary, the conventional suction hose 3 is passed through the flexible tube 2 up to the end and is provided via the plug connection 5 with a suction cannula. At the end of treatment, the suction hose 3 can again be drawn out of the flexible tube 2 and the screw clamp 9 removed.

Figure 3:
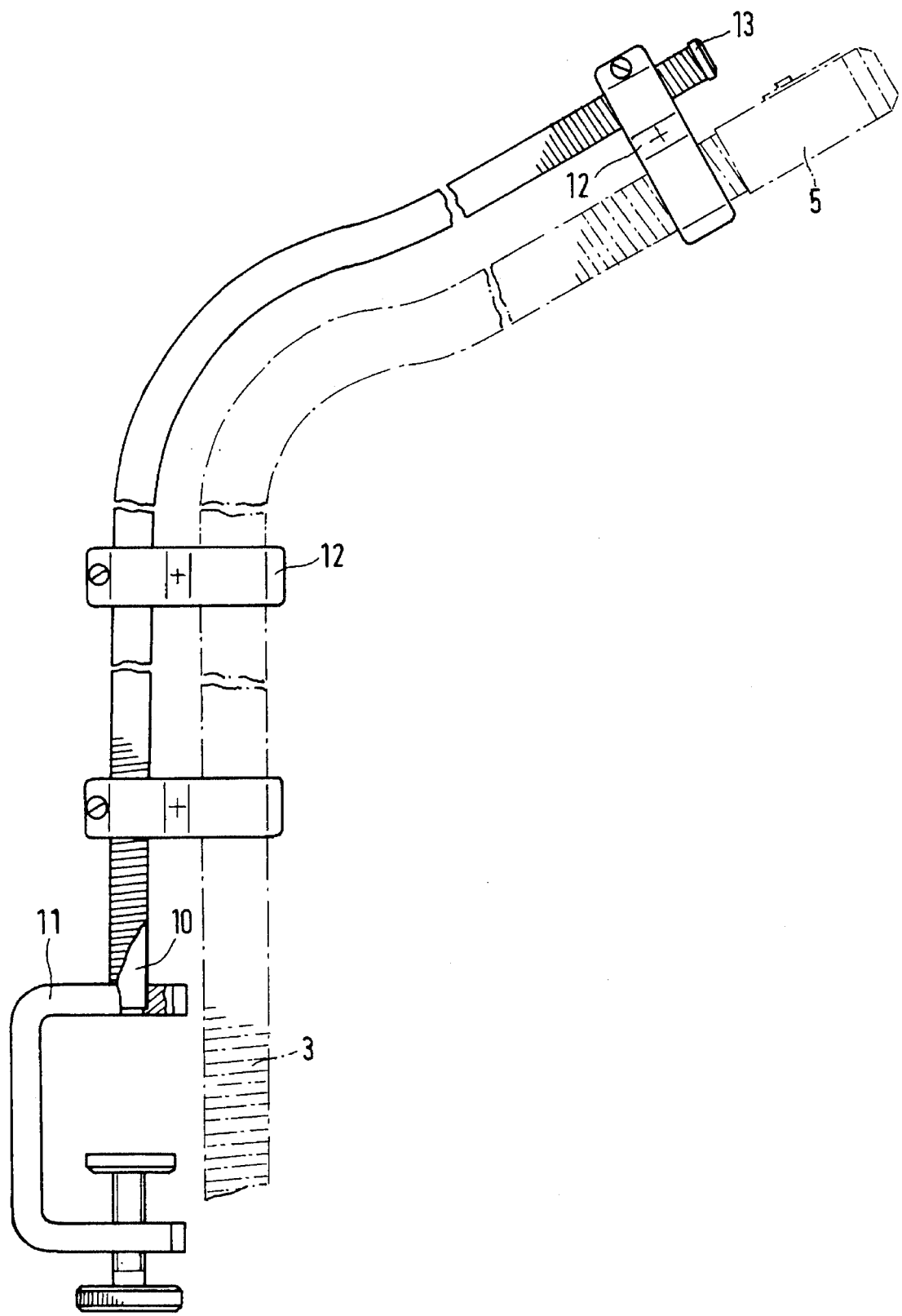
FIG. 3 is a partially cross sectioned side elevational view of a suction device according to a third embodiment of the invention.

FIG. 3 shows another embodiment of the suction tube 1 and existing dental treatment units can also be reequipped with Said suction device. In this case the suction device 1 has a flexible tube 10, which can be thinner, e.g., having an external diameter of 13 mm, than the flexible tube 2 of FIGS. 1 and 2. The flexible tube is bonded in a screw clamp 11 or is fixed therein in some other way. The screw clamp 11 is once again fixed to the existing treatment unit. Distributed over the length of the flexible tube 10 are several hose clips 12, to which the suction hose 3 of the suction device present on the treatment unit can be clipped. The flexible tube 10 is covered with an end cap 13. The hose clips 12 make it possible to detach the suction hose and use it in conjunction with the conventional suction device.

Figure 4:
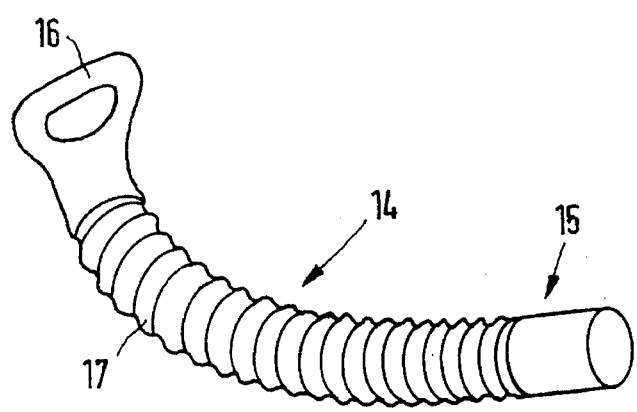
FIG. 4 is a plan view of a suction cannula.

A suction cannula 4 usable with the suction device 1 is shown in FIG. 4. It is fixed with one end 15 in the plug connection 5 of the suction hose 3 and the other end, constructed as a nozzle 16, is positioned in the mouth of the patient. The central part is shaped as a "flexible tube" or "flexible shaft" so that bending up to 90° is possible. Therefore the suction cannula 14 can be positioned more precisely in the mouth than the known, rigid suction cannulas. In order to improve the cleaning of the suction cannula or to remove deposits, the suction cannula 14 can be provided with a smooth internal lining.

In the case of existing treatment units, the suction device is switched on by means of a contact switch in the support located on the treatment unit, i.e., if the suction hose is removed from the support, the suction plant produces a vacuum. In the case of the suction device according to the invention, this contact switch is interrupted by means of the aforementioned pedal switch and the latter also switches on the suction plant.

I claim:

1. A suction device for a dental treatment unit comprising a plastic suction hose and a flexible suction cannula positioned intraorally and fixable thereto, wherein the suction hose is connected to a single three-dimensional movable, flexible tube and is guided in a fixed manner within the flexible tube.

2. The suction device according to claim 1, characterized in that the suction hose is removably guided within the flexible tube.

3. The suction device according to claim 1 characterized in that the flexible tube is installed in a fixed manner on the dental treatment unit.

4. The suction device according to claim 1 characterized in that the suction cannula is constructed as a three-dimensionally movable, flexible shaft.

5. The suction device of claim 4 wherein the suction cannula is fixed at one end to the suction hose.

6. The suction device of claim 5 wherein the suction cannula has a central part shaped as a flexible shaft allowing bending of the cannula up to 90°.

7. The suction device of claim 6, wherein the suction cannula has a smooth internal lining.

8. The suction device of claim 1, characterized in that the flexible tube is detachably connected to the dental treatment unit by means of a clamping device.

9. A suction device for a dental treatment unit comprising a plastic suction hose and a flexible suction cannula positioned intraorally and flexible thereto, wherein the suction hose is connected to a three-dimensional movable flexible tube and the suction hose is detachably fixed externally to the flexible tube.

10. A suction device for dental treatment units with a suction hose and a suction cannula to be positioned intraorally and fixable thereto, wherein the suction hose is connected to a three-dimensional movable, flexible tube, is detachably fixed externally to the flexible tube, and is fixed by means of hose clips to the flexible tube.

\* \* \* \* \*